United States Patent [19]

Mendelson et al.

[11] 4,057,585

[45] Nov. 8, 1977

[54] METHOD OF PREPARING 2,3-DICHLOROANISOLE

[75] Inventors: Wilford Lee Mendelson, Philadelphia; Robert Lee Webb, West Chester, both of Pa.

[73] Assignee: SmithKline Corporation, Philadelphia, Pa.

[21] Appl. No.: 719,795

[22] Filed: Sept. 2, 1976

[51] Int. Cl.² .............................................. C07C 41/04
[52] U.S. Cl. ................................................. 260/612 D
[58] Field of Search .................................... 260/612 D

[56] References Cited

U.S. PATENT DOCUMENTS

| | | | |
|---|---|---|---|
| 2,615,823 | 10/1952 | Lawlor et al. | 260/612 D X |
| 2,803,664 | 8/1957 | Redman | 260/612 D |

OTHER PUBLICATIONS

Cram et al., J.A.C.S., vol. 82 (1960) pp. 6412–6413.
Shaw et al., J. Org. Chem., vol. 41 (1976) pp. 732–733.
Finger et al., J.A.C.S., vol. 78 (1956) pp. 6034–6037.

*Primary Examiner*—Bernard Helfin
*Attorney, Agent, or Firm*—William H. Edgerton

[57] ABSTRACT

A new process for preparing 2,3-dichloroanisole comprises reacting 1,2,3-trichlorobenzene with an alkali metal methoxide preferably in the presence of methanol.

8 Claims, No Drawings

METHOD OF PREPARING 2,3-DICHLOROANISOLE

This invention comprises a new chemical process for preparing an important commercial chemical, 2,3-dichloroanisole. The process depends on the reaction of an alkali metal methoxide with 1,2,3-trichlorobenzene.

2,3-Dichloroanisole and its congeners are important intermediates for preparing pharmaceutical products such as ticrynafen (U.S. Pat. No. 3,758,506) or as ingredients in insecticides, weed controllers or plant hormones.

The prior art recognizes that alkali metal lower alkoxides react with unactivated aryl halides poorly. Chlorides particularly gave poor yields if unactivated by aromatic substitution such as by a nitro substituent in an ortho or para-position. A recent publication (J. E. Shaw et al., J. Org. Chem. 41, 732, 1976) has summarized the state of the art and also disclosed the reaction of mono and dichlorobenzenes with sodium methoxide in hexamethylphosphoramide as solvent. This solvent has been ruled hazardous as a carcinogen and should not be used commercially without special conditions.

We have now discovered that 1,2,3-trichlorobenzene, a compound having three unactivated chloro atoms will react with an alkali metal lower alkoxide to give substantial yields of the desired 2,3-dichloro-lower alkoxybenzene. Most usefully the reaction is carried out with sodium or potassium methoxide. Other alkali metal alkoxides such as lithium alkoxide may be used. Also if desired other alkoxides may be used such as alkali metal lower alkoxides of from 1-7 carbons, for example methoxide, butoxide, propoxide, isopropoxide, phenoxide, pentyloxide, isopentyloxide, hexyloxide. For practical purposes the most commercially useful agent, sodium methoxide, will be used for illustration of the invention.

Yields of the desired isomer run about two/thirds of theoretical, that is 65-75% of very pure product. The remaining material is the isomeric 2,6-dichloroanisole.

The reaction is carried out with about a stoichiometric amount of reactants or preferably an excess of the alkoxide. Usually about a 10-50% excess of alkoxide is used. The temperature and reaction time of the reaction are interdependent. For example, the reaction may be run at about 100°-120° C. for about 16-24 hours up to 175°-200° C. for ½ hour. Therefore the overall ranges are about 100°-200° C. for from about ½-24 hours. A range of from 110°-175° C. for ¼ to 1 hour has proved most useful. The progress of the reaction may be easily studied by gas chromatography during the reaction.

The alkoxide may be added in many forms such as the solid reactant itself or as an alcoholic solution. Sodium methoxide is most conveniently used as the commercially available 25% solution in methanol.

The solvent for the reaction is critical. For example, attempts to run the reaction in xylene at 144° C. for three hours only gave unreacted starting material as did reaction in formamide at 100° for 16 hours or at 160° for three hours. We have found that chemically inert solvents in which the reactants are substantially soluble or miscible and which have a dielectric constant of about 20-50 are essential to the reaction. For example dimethylformamide (DMF), dimethylacetamide (DMA), dimethylsulfoxide (DMS), sulfolane, glyme or mixtures of these solvents may be used. Preferred are dimethylacetamide, dimethylformamide and dimethylsulfoxide.

We have also unexpectedly found that the 60-70% yields or ⅔-⅓ isomer ratio can be altered significantly to obtain yields of about 85-95% of the desired 2,3-dichloroanisole isomer if a significant proportion of ethanol or preferably methanol is present in the reaction mixture. The methanol should be present in quantities to give a homogeneous reaction mixture. For convenience about 10-75% preferably 40-65% of the initial reaction mixture solvent should be methanol. The methanol is allowed to distill off the reaction mixture during reaction and may be optionally replaced as necessary. The alcohol must always be present in sufficient quantities to solvate the unreacted metal alkoxide. Since the various chloroalkoxybenzenes can be purified easily by fractional distillation any trichlorobenzene containing starting material may be used.

The reaction mixture after completion of the reaction as studied by gas chromatography is worked up by standard procedures. For example the mixture is cooled and quenched in an excess of water. The organic material is extracted into an immisable organic liquid such as ether, toluene, benzene or xylene. After washing, drying and evaporating the extracts the product is isolated from the residue by distillation. Residual product left unextracted can be obtained by extraction with a second organic solvent such a methylene chloride. The solvents may be recovered by known techniques.

The reaction may be represented as follows:

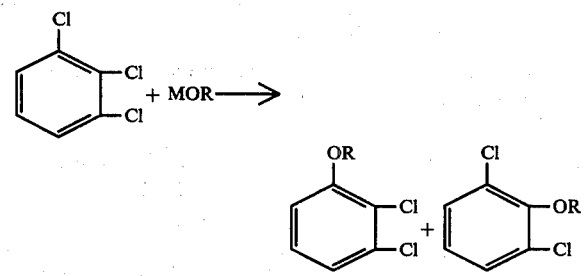

in which M is an alkali metal preferably sodium or potassium and R is lower alkyl of 1-7 carbon atoms or phenyl.

The following examples are intended to further illustrate specific embodiments of this invention. All melting points are Centigrade.

EXAMPLE 1

The trichlorobenzene-solvent mixture is heated to 60°. Solid sodium methoxide is added over one minute then the oil bath temperature is raised to 95°-100° C. for 16 hours. The cooled reaction mixture is poured into 100 ml of water. The quenched mixture is extracted with ether and petroleum ether repeatedly. The dried extracts are evaporated and the residue examined by gas chromatography with the following results:

| Trichloro benzene (g) | Sodium methoxide (g) | Solvent (ml) | Temp. time | Crude yield | Ratio* isomers | Comments |
|---|---|---|---|---|---|---|
| 3.62 (20 mm) | 1.30 (24 mm) | formamide | 100°/16 hr | 0% | — | dark; no product |

-continued

| Trichloro benzene (g) | Sodium methoxide (g) | Solvent (ml) | Temp. time | Crude yield | Ratio* isomers | Comments |
|---|---|---|---|---|---|---|
| 3.62 | 1.30 | DMF 40 | 110°/16 hr | 70% | >2.04/1 | — |
| 14.5 | 5.60 | DMA 130 | 110°/115° 16 hr | 82% | >2.2/1 | — |
| 3.62 | 1.30 | DMS/HMPA 30/15 | 110°/16 hr | 65% | >1.54/1 | — |
| 3.62 | 1.30 | sulfolane | 110°/16 hr | 65% | >1.54/1 | — |

*2,3 isomer: 2,6 isomer

EXAMPLE 2

Quantities
Trichlorobenzene — 363 g
Sodium methoxide — 650 ml 25% commercial solution in methanol
Dimethyl acetamide — 660 ml
Procedure Trichlorobenzene (363 g, 2 moles) was dissolved in 600 ml of dimethyl acetamide and 650 ml of 25% sodium methoxide in methanol solution added all at once. The solution was stirred and heated to 166° as the methanol slowly distilled out. The solution was held at 166° for 30 minutes, * cooled and quenched with 5 times its volume of water and extracted with toluene (2 × 1000 ml). The toluene extracts were washed with water (1 L) and dried over sodium sulfate. The toluene was removed by distillation under reduced pressure and the residue fractionated to yield the pure 2,3-dichloroanisole, bp 140°/28 mm. Yield 212 g (60%). Considerable material remains in the aqueous DMAC layer and can be recovered by repeated extractions with methylene chloride.
*G.C. showed an isomer ratio of 92:8 for the 2,3:2,6 isomers.

EXAMPLE 3

Following the precedures of the above examples the following results were obtained.

| Solvent | Methoxide Form* | Temp | Time | Isomer Ratio+ |
|---|---|---|---|---|
| DMA | solid | 166° | 30 min | 70:30 |
| DMA | 25% in methanol | 160° | 6 hrs | 92:8 |
| DMF | 25% in methanol | 155 | 2 hrs | 72:28⊕ |
| xylene | solid | 144° | 3 hrs | only starting material |
| Formamide | 25% in methanol | 160 | 3 hrs | mostly starting material |
| DMF | solid | 155 | 1 hr | 70:30 |

*either as solid sodium methoxide or commercial 25% solution in methanol.
+2,3 isomer: 2,6-isomer
⊕contains some starting material

EXAMPLE 4

The following alkoxides may be substituted for the sodium methoxide of Example 2: potassium methoxide, lithium ethoxide, sodium phenoxide, potassium pentyloxide, sodium heptyloxide, sodium isopropoxide, potassium propoxide and sodium butoxide. These give the corresponding known 2,3-dichloro-1-alkoxybenzenes.

EXAMPLE 5

363 g (1 mole) of 1,2,3-trichlorobenzene is dissolved in 600 ml dimethyl acetamide and heated to 125° with stirring. 500 ml of 25% commercial sodium methoxide in methanol is then added at such a rate that the temperature is maintained at 125°-130°. After addition is complete the temperature is maintained at 130° for 30 minutes. The mixture is diluted with water and extracted with toluene. The toluene extracts are washed with brine, dried and the toluene removed by distillation. The residue is fractionated to yield 200 g of the desired isomer 2,3-dichloroanisole bp 140°/29 mm. By appropriate fractionation the minor isomer 2,3-dichloroanisole may also be obtained.

Dimethylformamide and dimethylsulfoxide may also be used with only slight variations in yield.

What is claimed is:

1. The method of preparing 2,3-dichloro-1-loweralkoxybenzenes comprising the reaction of 1,2,3-trichlorobenzene with an alkali metal lower alkoxide with heating at about 100°-200° C. for from about ½-24 hours in an inert organic solvent selected from the group consisting of dimethylformamide, dimethyl acetamide and dimethylsulfoxide and additionally in the presence of an alkanol selected from the group consisting of methanol and ethanol and said alkanol is present in the reaction mixture in a quantity sufficient to solvate the metal lower alkoxide reagent.

2. The method of claim 1 in which the metal alkoxide is sodium or potassium methoxide or ethoxide.

3. The method of claim 2 in which the metal alkoxide is sodium or potassium methoxide.

4. The method of claim 1 in which methanol is present in the reaction mixture in a quantity sufficient to solvate the metal lower alkoxide reagent.

5. The method of claim 2 in which methanol is present in the reaction mixture in a quantity sufficient to solvate the sodium or potassium methoxide or ethoxide.

6. The method of claim 3 in which methanol is present in the reaction material at about 40-60% of the initial solvent system.

7. The method of claim 1 in which the alkoxide is sodium methoxide, the solvent is dimethylacetamide, the temperature of the reaction is at from about 100°-175°, the time of the reaction is from about ¼-1 hour and methanol is present in about 50-75% of said solvent.

8. In the method of reacting 1,2,3-trichlorobenzene with sodium or potassium methoxide in dimethylacetamide, dimethylformamide or dimethylsulfoxide as solvent at temperatures of from 100°-200° until the reaction is complete, the improvement comprising adding to the reaction mixture a quantity of methanol sufficient to solvate said methoxide throughout the reaction.

* * * * *